(12) United States Patent
Haynes et al.

(10) Patent No.: US 8,076,334 B2
(45) Date of Patent: Dec. 13, 2011

(54) PRODRUGS OF THYROID HORMONE ANALOGS

(75) Inventors: Nancy-Ellen Haynes, Cranford, NJ (US); Nathan Scott, Livingston, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 678 days.

(21) Appl. No.: 12/202,552

(22) Filed: Sep. 2, 2008

(65) Prior Publication Data

US 2009/0082310 A1    Mar. 26, 2009

Related U.S. Application Data

(60) Provisional application No. 60/973,846, filed on Sep. 20, 2007.

(51) Int. Cl.
*A61K 31/53* (2006.01)
*C07D 403/10* (2006.01)

(52) U.S. Cl. .............. 514/242; 514/247; 514/252.05; 544/182; 544/238; 544/239

(58) Field of Classification Search .......... 514/242, 514/247, 252.05; 544/182, 238, 239
See application file for complete search history.

(56) References Cited

U.S. PATENT DOCUMENTS

| 4,188,388 A | 2/1980 | Thuillier, born Nachmias et al. |
| 5,284,971 A | 2/1994 | Walker et al. |

FOREIGN PATENT DOCUMENTS

| EP | 188351 | 7/1986 |
| EP | 728482 | 8/1996 |
| WO | WO 9702023 | 1/1997 |
| WO | WO 9857919 | 12/1998 |
| WO | WO 9900353 | 1/1999 |
| WO | WO 2005051298 | 6/2005 |
| WO | WO 2007/009913 A1 | 1/2007 |

OTHER PUBLICATIONS

Paul M. Yen Physiological Review, vol. 81(3): pp. 1097-1126 (2001).
M.A. Lazar Endocrine Reviews, vol. 14: pp. 348-399 (1993).
Abel et. al. J. Clin. Invest., vol. 104: pp. 291-300 (1999).
B. Gloss et. al. Endocrinology, vol. 142: pp. 544-550 (2001).
C. Johansson et. al. Am. J. Physiol., vol. 275: pp. R640-R646 (1998).
Paul Webb Expert Opin. Investig. Drugs, vol. 13(5): pp. 489-500 (2004).
Eugene Morkin et. al. Journal of Molecular and Cellular Cardiology, vol. 37: pp. 1137-1146 (2004).
J.J. Abrams et. al. J. Lipid Res., vol. 22: pp. 323-338 (1981).
M. Aviram et. al. Clin. Biochem., vol. 15: pp. 62-66 (1982).
Gene C. Ness et. al. Biochemical Pharmacology, vol. 56: pp. 121-129 (1998).
G.J. Grover et. al. Endocrinology, vol. 145: pp. 1656-1661 (2004).
G.J. Grover et. al. Proc. Natl. Acad. Sci. USA, vol. 100: pp. 10067-10072 (2003).
De Bruin et. al. J. Clin. Endo. Metab., vol. 76: pp. 121-126 (1993).
A.H. Underwood et al. Nature, vol. 324 pp. 425-429 (1986).
Thomas S. Scalan Current Opinion in Drug Discovery & Development, vol. 4 (5): pp. 614-622 (2001).
Malm Johan Current Pharmaceutical Design, vol. 10(28): pp. 3525-3532 (2004).
Expert Opin. Ther. Patents, vol. 14: pp. 1169-1183 (2004).
Teruomi et. al. Agricultural and Biological Chemistry, vol. 38(6): pp. 1169-1176 (1974).
P.D. Leeson et. al. J. Med. Chem.vol. 32: pp. 320-326 (1989).
Valentino, Stella, Advanced Drug Delivery Reviews XP002080432, (1989).
Fleisher D, Improved oral drug delivery XP002389735, (1996).
Simplicio, Ana Molecules, XP 002503564, (1996).

*Primary Examiner* — Paul V. Ward
(74) *Attorney, Agent, or Firm* — George W. Johnston; Dennis P. Tramaloni; Samuel H. Megerditchian

(57) ABSTRACT

Provided herein are compounds of the formula (I):

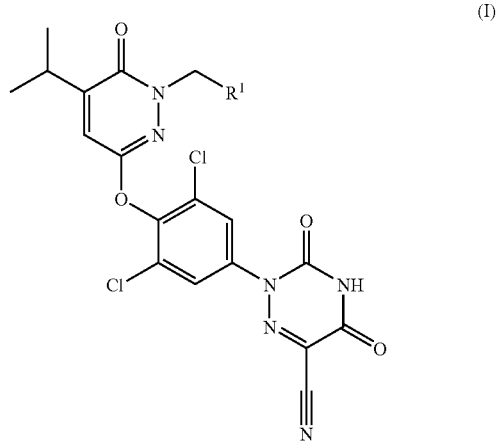

(I)

as well as pharmaceutically acceptable salts thereof, wherein the substituents are as those disclosed in the specification. These compounds, and the pharmaceutical compositions containing them, are useful for the treatment of diseases such as obesity, hyperlipidemia, hypercholesterolemia and diabetes and other related disorders and diseases, and may be useful for other diseases such as NASH, atherosclerosis, cardiovascular diseases, hypothyroidism, thyroid cancer and other disorders and diseases related thereto.

18 Claims, No Drawings

PRODRUGS OF THYROID HORMONE ANALOGS

PRIORITY TO RELATED APPLICATION(S)

This application claims the benefit of U.S. Provisional Application No. 60/973,846, filed Sep. 20, 2007, which is hereby incorporated by reference in its entirety.

FIELD OF THE INVENTION

The present invention is directed to prodrugs of novel thyroid receptor ligands, particularly to pyridazinone analogs. The invention is also directed to pharmaceutical compositions having these prodrugs and methods of their use for the treatment of metabolic diseases such as obesity, hyperlipidemia, hypercholesterolemia and diabetes. Such compounds may also be useful for the treatment of nonalcoholic steatohepatitis (NASH), liver steatosis, atherosclerosis, cardiovascular diseases, hypothyroidism, thyroid cancer and related disorders and diseases.

All documents cited or relied upon below are expressly incorporated herein by reference.

BACKGROUND OF THE INVENTION

Thyroid hormones are critical for normal growth and development and for maintaining metabolic homeostasis (Paul M. Yen Physiological Review, Vol. 81(3): pp. 1097-1126 (2001)). Circulating levels of thyroid hormones are tightly regulated by feedback mechanisms in the hypothalamus/pituitary/thyroid (HPT) axis. Thyroid dysfunction leading to hypothyroidism or hyperthyroidism clearly demonstrates that thyroid hormones exert profound effects on cardiac function, body weight, metabolism, metabolic rate, body temperature, cholesterol, bone, muscle and behavior.

Thyroid hormone is produced by the thyroid gland and secreted into circulation as two distinct forms, 3,5,3',5'-tetra-iodo-L-thyronine (T4) and 3,5,3'-tri-iodo-L-thyronine (T3). While T4 is the predominant form secreted by the thyroid gland, T3 is the more biologically active form. T4 is converted to T3 by tissue specific deiodinases in all tissues but predominantly in the liver and kidney. The biological activity of thyroid hormones is mediated by thyroid hormone receptors (TRs) (M. A. Lazar Endocrine Reviews, Vol. 14: pp. 348-399 (1993)). TRs belong to the superfamily known as nuclear receptors. TRs form heterodimers with the retinoid receptor that act as ligand-inducible transcription factors. TRs have a ligand binding domain, a DNA binding domain, and an amino terminal domain, and regulate gene expression through interactions with DNA response elements and with various nuclear co-activators and co-repressors. The thyroid hormone receptors are derived from two separate genes, α and β. These distinct gene products produce multiple forms of their respective receptors through differential RNA processing. The major thyroid receptor isoforms are α1, α2, β1 and β2. Thyroid hormone receptors α1, β1 and β2 bind thyroid hormone. It has been shown that the thyroid hormone receptor subtypes can differ in their contribution to particular biological responses. Recent studies suggest that TRβ1 plays an important role in regulating TRH (thyrotropin releasing hormone) and on regulating thyroid hormone actions in the liver. TRβ2 plays an important role in the regulation of TSH (thyroid stimulating hormone) (Abel et. al. J. Clin. Invest., Vol 104: pp. 291-300 (1999)). TRβ1 plays an important role in regulating heart rate (B. Gloss et. al. Endocrinology, Vol. 142: pp. 544-550 (2001); C. Johansson et. al. Am. J. Physiol., Vol. 275: pp. R640-R646 (1998)).

Some of the effects of thyroid hormones may be therapeutically beneficial if adverse effects can be minimized or eliminated (Paul M. Yen Physiological Reviews, Vol. 81(3): pp. 1097-1126 (2001); Paul Webb Expert Opin. Investig. Drugs, Vol. 13(5): pp. 489-500 (2004)). For example, thyroid hormones increase metabolic rate, oxygen consumption and heat production and thereby reduce body weight. Reducing body weight will have a beneficial effect in obese patients by ameliorating the co-morbidities associated with obesity, and may also have a beneficial effect on glycemic control in obese patients with Type 2 diabetes.

Another therapeutically beneficial effect of thyroid hormone is the lowering of serum low density lipoprotein (LDL) (Eugene Morkin et. al. Journal of Molecular and Cellular Cardiology, Vol. 37: pp. 1137-1146 (2004)). It has been found that hyperthyroidism is associated with low total serum cholesterol, which is attributed to thyroid hormone increasing hepatic LDL receptor expression and stimulating the metabolism of cholesterol to bile acids (J. J. Abrams et. al. J. Lipid Res., Vol. 22: pp. 323-38 (1981)). Hypothyroidism, in turn, has been associated with hypercholesterolemia and thyroid hormone replacement therapy is known to lower total cholesterol (M. Aviram et. al. Clin. Biochem., Vol. 15: pp. 62-66 (1982); J. J. Abrams et. al. J. Lipid Res., Vol. 22: pp. 323-38 (1981)). Thyroid hormone has been shown in animal models to have the beneficial effect of increasing HDL cholesterol and improving the ratio LDL to HDL by increasing the expression of apo A-1, one of the major apolipoproteins of HDL (Gene C. Ness et. al. Biochemical Pharmacology, Vol. 56: pp. 121-129 (1998); G. J. Grover et. al. Endocrinology, Vol. 145: pp. 1656-1661 (2004); G. J. Grover et. al. Proc. Natl. Acad. Sci. USA, Vol. 100: pp. 10067-10072 (2003)). Through its effects on LDL and HDL cholesterol, it is possible that thyroid hormones may also lower the risk of atherosclerosis and other cardiovascular diseases. The incidence of atherosclerotic vascular disease is directly related to the level of LDL cholesterol. Additionally, there is evidence that thyroid hormones lower Lipoprotein (a), an important risk factor which is elevated in patients with atherosclerosis (Paul Webb Expert Opin. Investig. Drugs, Vol. 13(5): pp. 489-500 (2004); de Bruin et. al. J. Clin. Endo. Metab., Vol. 76: pp. 121-126 (1993)).

With the incidence of obesity and its co-morbidities, diabetes, metabolic syndrome, and atherosclerotic vascular disease rising at epidemic rates, the utility of compounds capable of treating these diseases would be highly desirable. To date, the therapeutic uses of the naturally occurring thyroid hormone have been limited by the adverse side effects associated with hyperthyroidism, especially cardiovascular toxicity.

Therefore, efforts have been made to synthesize thyroid hormone analogs which exhibit increased thyroid hormone receptor beta selectivity and/or tissue selective action. Such thyroid hormone mimetics may yield desirable reductions in body weight, lipids, cholesterol, and lipoproteins, with reduced impact on cardiovascular function or normal function of the hypothalamus/pituitary/thyroid axis (A. H. Underwood et al. Nature, Vol. 324: pp. 425-429 (1986), G. J. Grover et. al. PNAS, Vol. 100: pp. 10067-10072 (2003); G. J. Grover Endocrinology, Vol. 145: pp. 1656-1661(2004); Yi-lin Li et. al. PCT Int. Appl. WO 9900353 (1999); Thomas S. Scanlan et. al. PCT Int. Appl. WO 9857919 (1998); Keith A. Walker et. al. U.S. Pat. No. 5,284,971 (1994); Mark D. Erion et. al. PCT Int. Appl. WO 2005051298 (2005); Malm Johan Current Pharmaceutical Design, Vol. 10(28): pp. 3525-3532 (2004);

Expert Opin. Ther. Patents, Vol. 14: pp. 1169-1183 (2004); Thomas S. Scalan Current Opinion in Drug Discovery & Development, Vol. 4 (5): pp. 614-622 (2001); Paul Webb Expert Opinion on Investigational Drugs, Vol. 13 (5): pp. 489-500 (2004)).

The development of thyroid hormone analogs which avoid the undesirable effects of hyperthyroidism and hypothyroidism while maintaining the beneficial effects of thyroid hormones would open new avenues of treatment for patients with metabolic diseases such as obesity, hyperlipidemia, hypercholesterolemia, diabetes and other disorders and diseases such as liver steatosis and NASH, atherosclerosis, cardiovascular diseases, hypothyroidism, thyroid cancer, thyroid diseases, and related disorders and diseases.

Pyridazinone compounds that are structurally different from the compounds of the present invention have been previously disclosed (Teruomi et. al. Agricultural and Biological Chemistry, Vol. 38(6): pp. 1169-76 (1974); P. D. Leeson et. al. J. Med. Chem. Vol. 32: pp. 320-326 (1989); Eur. Pat. Appl. EP 188351 (1986); Damien John Dunnington PCT Int. Appl. WO 9702023 (1997); and Eur. Pat. Appl. EP 728482 (1996)).

There is still a need, however, for novel thyroid hormone prodrugs such as, for example, novel pyridazinone prodrugs, that have the beneficial effects of thyroid hormone while avoiding the undesirable effects.

SUMMARY OF THE INVENTION

In an embodiment of the present invention, provided is a compound of formula (I)

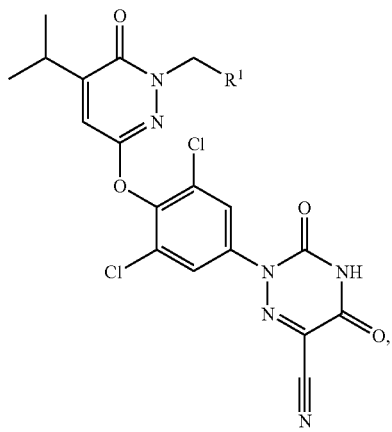

(I)

wherein:

$R^1$ is —OH, O-linked amino acid, —OP(O)(OH)$_2$ or —OC(O)—$R^2$;

$R^2$ is lower alkyl, alkoxy, alkyl acid, cycloalkyl, heterocycloalkyl, —(CH$_2$)$_n$—heterocycloalkyl, aryl, heteroaryl, or —(CH$_2$)$_n$-heteroaryl; and n is 0 or 1;

or a pharmaceutically acceptable salt thereof.

In another embodiment of the present invention, provided is a pharmaceutical composition comprising a therapeutically effective amount of a compound according to formula (I), or a pharmaceutically acceptable salt thereof, and a pharmaceutically acceptable carrier.

DETAILED DESCRIPTION OF THE INVENTION

The invention provides for compounds of formula (I),

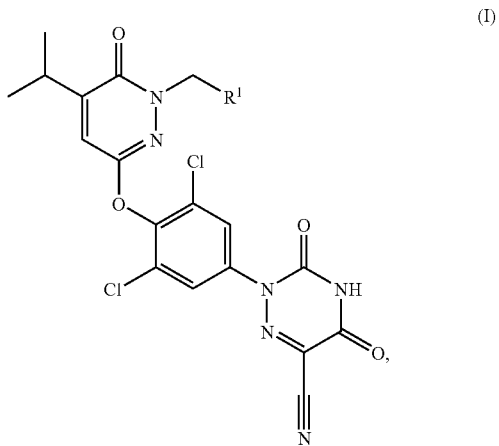

(I)

which are prodrugs of the compound of formula (Ia):

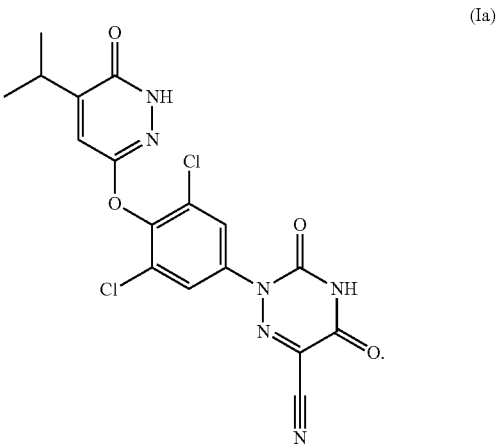

(Ia)

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

The term "prodrug" refers to compounds, which undergo transformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and/or enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions. A useful reference is Prodrugs; Challenges and Rewards, Volumes 1 and 2, V. Stella, R. T. Borchardt, M. J. Hageman, R. Oziyai, H. Maag, and J. W. Tilley, editors, Springer, 2007.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent carbocyclic radical of three to seven, preferably three to six carbon atoms. This term is further exemplified by radicals such as cyclopropyl, cyclobutyl, cyclopentyl and cyclohexyl. In a preferred embodiment, the "cycloalkyl" moieties can optionally be substituted with one, two, three or four substituents, wherein each substituent is independently, for example, hydroxy, alkyl, alkoxy, halogen or amino, unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a cyclic alkyl ring, wherein one, two or three of the carbon ring atoms is replaced by a heteroatom such as N, O or S. Examples of heterocycloalkyl groups include, but are not limited to, morpholine, thiomorpholine, piperazine, piperidine and the like. The heterocycloalkyl groups may be unsubstituted or substituted.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic monovalent mono- or polycarbocyclic radical, such as phenyl or naphthyl, preferably phenyl.

The alkyl and aryl groups may be substituted or unsubstituted. Where substituted, there will generally be, for example, one to three substituents present, preferably one substituent. Substituents may include, for example: carbon-containing groups such as alkyl, aryl, arylalkyl (e.g. substituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (such as "alkyl acid" when an acid substituent is on an alkyl group, preferably acetic, propionic and butanoic), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono-or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups.

The term "heteroaryl," alone or in combination with other groups, means a monocyclic or bicyclic radical of five to twelve ring atoms having at least one aromatic ring containing one, two, or three ring heteroatoms selected from N, O, and S, the remaining ring atoms being C. One or two ring carbon atoms of the heteroaryl group may be replaced with a carbonyl group. The heteroaryl group described above may be substituted independently with one, two, or three substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The lower alkyl groups may be substituted or unsubstituted, preferably unsubstituted. Where substituted, there will generally be, for example, one to three substitutents present, preferably one substituent.

As used herein, the term "alkoxy" means alkyl-O-; and "alkoyl" means alkyl-CO—. Alkoxy substituent groups or alkoxy-containing substituent groups may be substituted by, for example, one or more alkyl groups.

As used herein, the term "halogen" means a fluorine, chlorine, bromine or iodine radical, preferably a fluorine, chlorine or bromine radical, and more preferably a fluorine or chlorine radical.

As used herein, the term "O-linked amino acid" means any amino acid, naturally occurring or synthetic, linked to a molecule via an oxygen of a carboxyl group of said amino acid, preferably via the carboxyl group of the carboxy terminus of said amino acid.

"Pharmaceutically acceptable salt" refers to conventional acid-addition salts or base-addition salts that retain the biological effectiveness and properties of the compounds of formula I and are formed from suitable organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable ester" refers to a conventionally esterified compound of formula I having a carboxyl group, which esters retain the biological effectiveness and properties of the compounds of formula I and are cleaved in vivo to the corresponding active carboxylic acid. Examples of ester groups which are cleaved (in this case hydrolyzed) in vivo to the corresponding carboxylic acids are those in which the hydrogen is replaced with lower alkyl which is optionally substituted, e.g., with a heterocycle, cycloalkyl, etc. Examples of substituted lower alkyl esters are those in which lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, $-C(O)NH_2$ is analogous to an ester, as the $-NH_2$ may be cleaved in vivo and replaced with a hydroxy group, to form the corresponding carboxylic acid.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The "therapeutically effective amount" or "dosage" of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of from about 0.01 mg/kg to about 50 mg/kg should be appropriate, although the upper limit may be exceeded when indicated. The dosage is preferably from about 0.3 mg/kg to about 10 mg/kg per day. A preferred dosage may be from about 0.70 mg/kg to about 3.5 mg/kg per day. The daily dosage can be administered as a single dose or in divided doses, or for parenteral administration it may be given as continuous infusion.

Compounds of the present invention can be prepared beginning with commercially available starting materials and utilizing general synthetic techniques and procedures known to those skilled in the art. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; and Multigram II Mettler Toledo Instrument Newark, Del. Biotage and ISCO columns are prepacked silica gel columns used in standard chromatography. Chemicals may be purchased from companies such as for example Aldrich, Argonaut Technologies, VWR and Lancaster. Outlined below are reaction schemes suitable for preparing such compounds. Further exemplification is found in the specific Examples detailed below.

Scheme 1

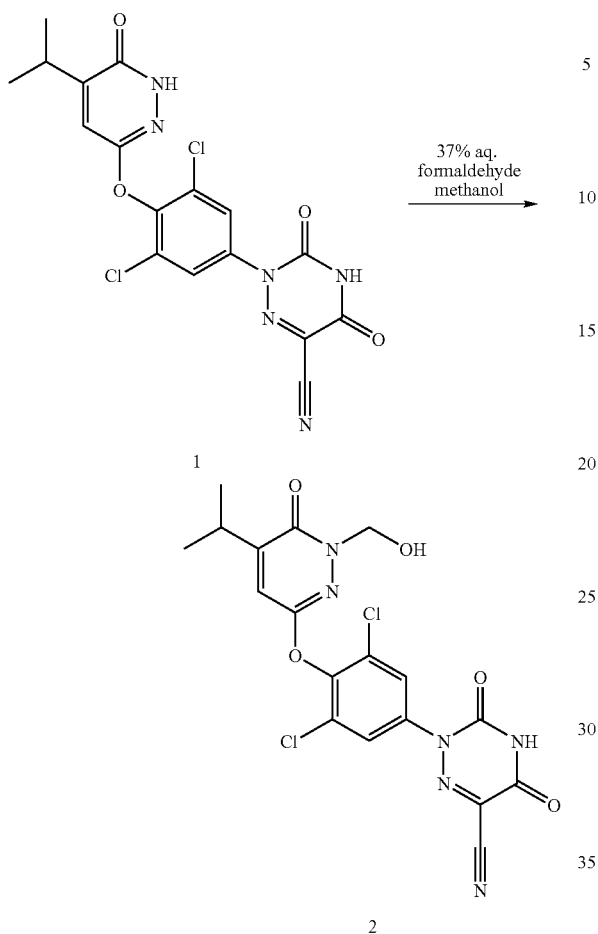

The synthesis for compound 1 was prepared as described in Haynes, N-E., et. al. PCT Int. Appl. (2007) WO 009913A1. The synthesis for compound 2 is outlined in scheme 1. Compound 1 was treated with aqueous formaldehyde in methanol at elevated temperatures to give compound 2 (scheme 1) (see for example, Dunn, J. P., et. al. PCT Int. Appl. (2005) WO 090317A1).

Scheme 2

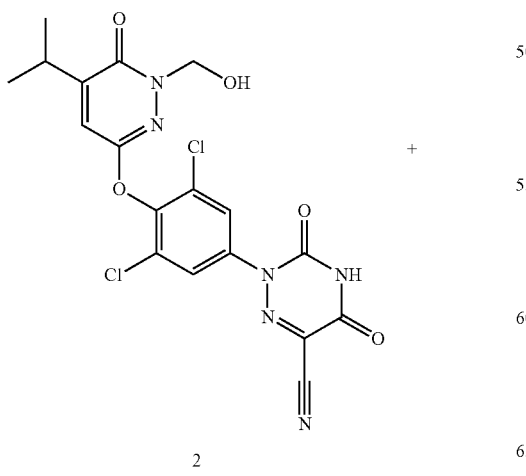

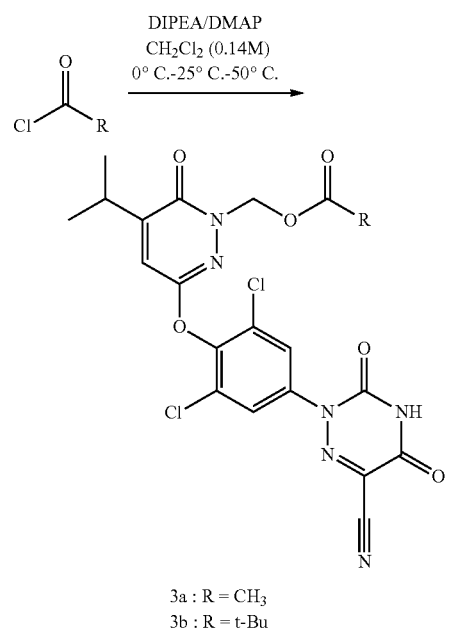

3a : R = $CH_3$
3b : R = t-Bu
3c : R = propyl
3d : R = $CH(CH_3)_2$
3e : R = morpholine
3f : R = phenyl
3g : R = pyrazine
3h : R = pyrimidine
3i : R = ethyl
3j : R = $CH_2$-N-methyl piperizine
3k : $CH_2$-morpholine Compounds 3a-k were synthesized following the reaction outlined in scheme 2. Compound 2 was treated with base and 4-N,N-dimethylaminopyridine followed by various acid chlorides to give compounds 3a-k (see for example, Dunn, J. P., et. al. PCT Int. Appl. (2005) WO 090317A1).

Scheme 3

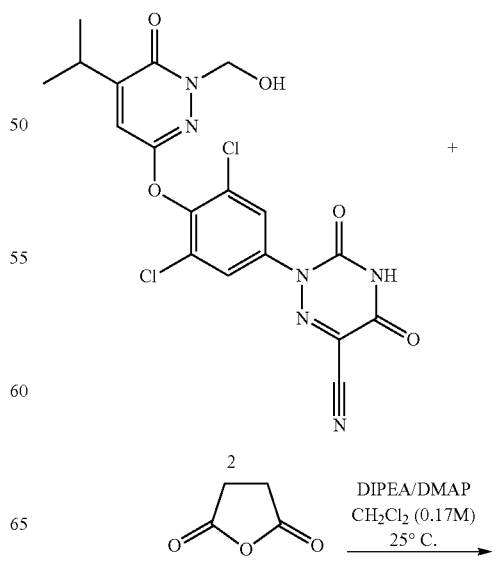

-continued

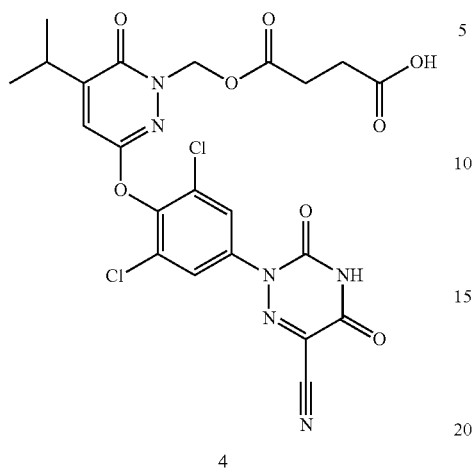

4

Compound 4 was synthesized following the reaction outlined in scheme 3. Compound 2 was treated with base and 4-N,N-dimethylaminopyridine followed by succinic anhydride to give compound 4 (see for example, Dunn, J. P., et. al. PCT Int. Appl. (2006) US 0025462A1)

Scheme 4

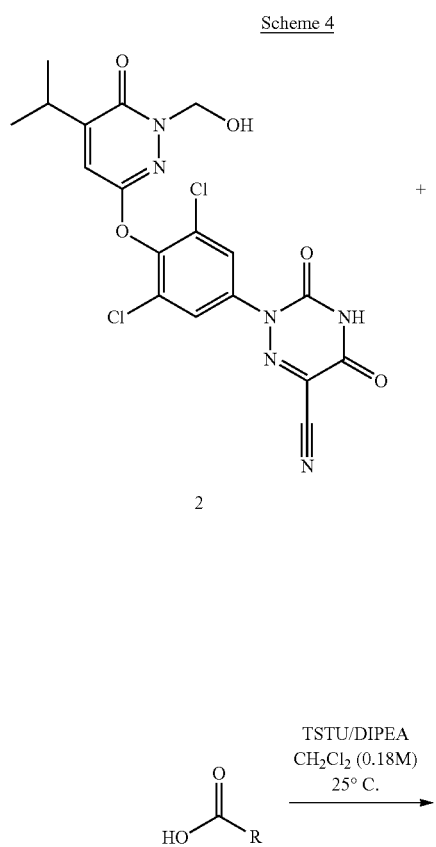

-continued

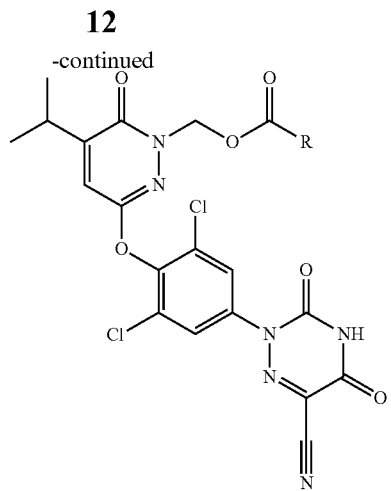

5a: R = CH₂-3-pyridine
5b: R = 3-pyridine

Compounds 5a and 5b were synthesized following the reaction outlined in scheme 4. The acid was activated with N,N,N',N'-tetramethyl-O—(N-succinimidyl)uronium tetrafluoroborate and base followed by treatment with of pyridin-3-yl-acetic acid and isonicotinic acid to give compounds 5a and b respectively (see for example, Bannwarth, W., et. al., Tet. Lett., 1991, 32(9), 1157-1160).

Scheme 5

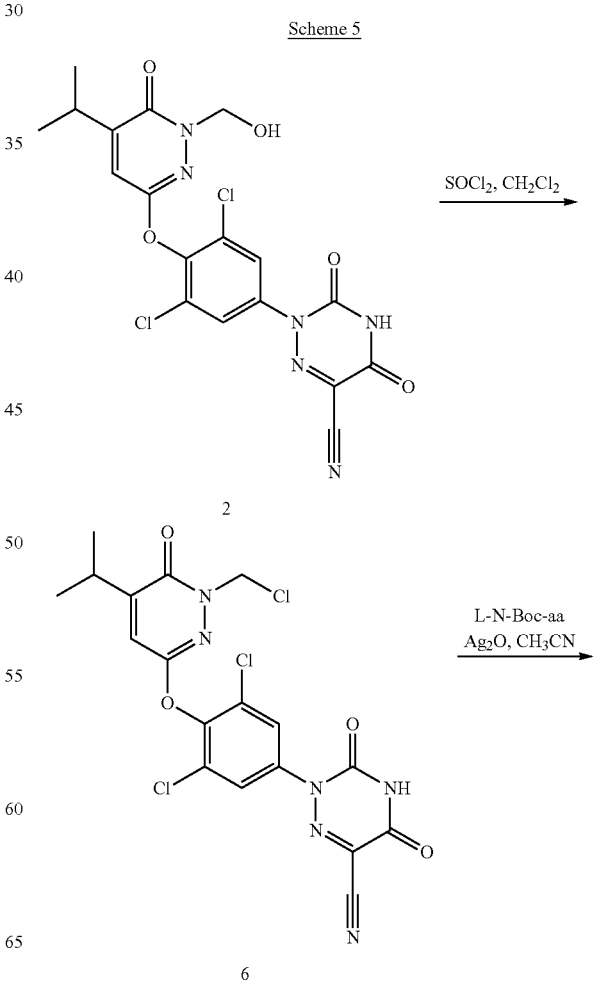

Scheme 6

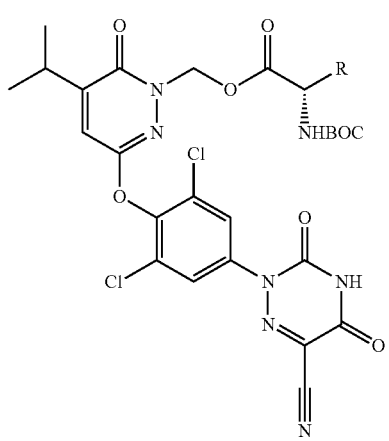

7a : R = CH(CH$_3$)$_2$
7b : R = CH(CH$_3$)Et

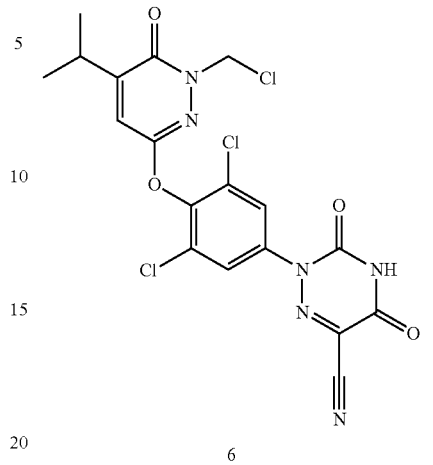

6

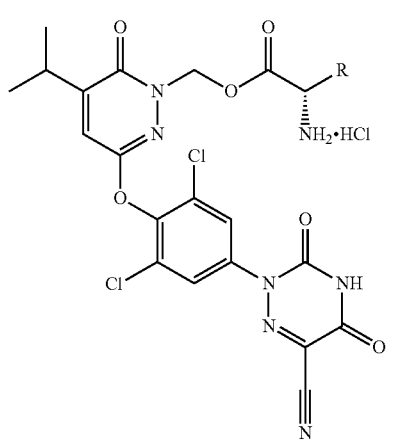

8a : R = CH(CH$_3$)$_2$
8b : R = CH(CH$_3$)Et

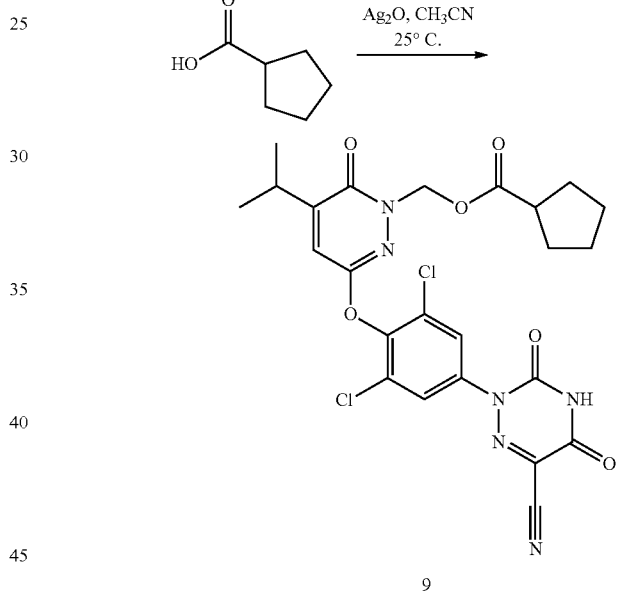

9

Compound 9 was synthesized following the reaction outlined in scheme 6. The chloride of compound 6 was displaced with cyclopentanecarboxylic acid in the presence of silver (I) oxide (see for example, Ermolenko, L., et. al., *J. Org. Chem*, 2006, 71(2), 693-703).

Compounds 8a and 8b were synthesized following the reactions outlined in scheme 5. The hydroxyl group of compound 2 was converted to the chloro derivative (see for example, Pesquet, A., et. al., *Org. and Biomol. Chem.*, 2005, 3(21), 3937-3947). The chloride of compound 6 was displaced with the respective N-tert-butoxycarbonyl protected amino acid in the presence of silver (I) oxide (see for example, Ermolenko, L., et. al., *J. Org. Chem*, 2006, 71(2), 693-703). Removal of the tert-butyloxy protecting group under acidic condition afforded compounds 8a and 8b (see for example, Dunn, J. P., et. al. PCT Int. Appl. (2005) WO 090317A1).

Scheme 7

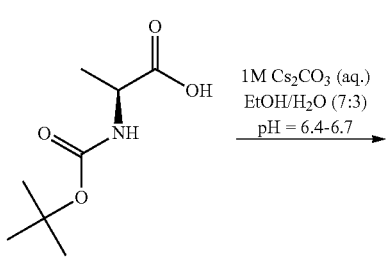

1M Cs$_2$CO$_3$ (aq.)
EtOH/H$_2$O (7:3)
pH = 6.4-6.7

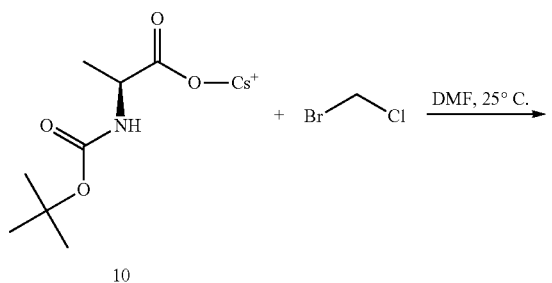

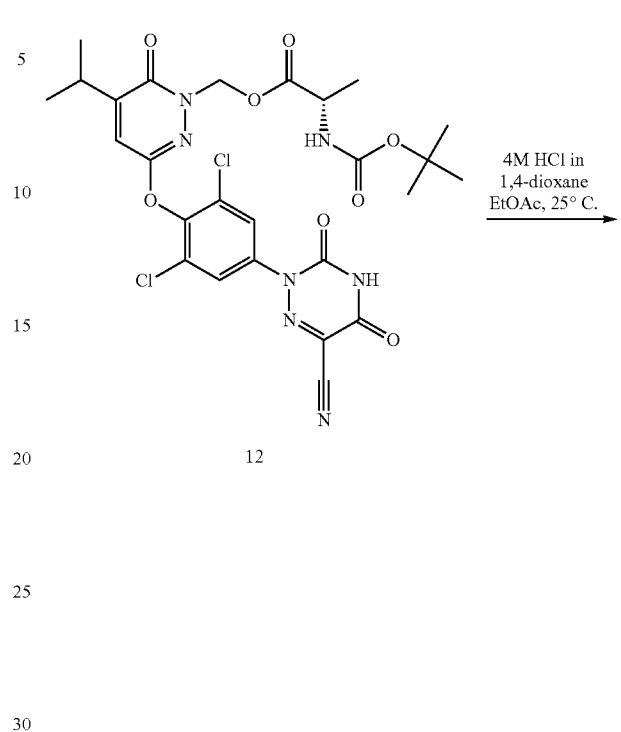

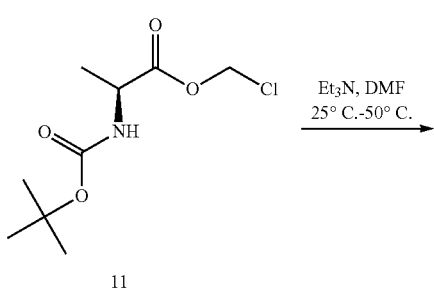

Compound 12 was synthesized following a series of reactions outlined in scheme 7. The chloro-methyl ether, compound 11, was prepared by first generating the cesium salt of the starting material, (S)-2-tert-butoxycarbonylamino-propionic acid, followed by displacement of the bromide of bromo-chloro-methane using the procedure described by Gomes, P., et. al., *Syn. Comm.,* 2003, 33(10), 1683-1693. The chloride of compound 11 was then displaced by the pyridazinone amine of compound 1 under basic conditions to afford compound 12 (see for example, Gomes, P., et. al., *Syn. Comm.,* 2003, 33(10), 1683-1693). Removal of the tert-butyloxy protecting group under acidic condition afforded compound 12 (see for example, Dunn, J. P., et. al. PCT Int. Appl. (2005) WO 090317A1).

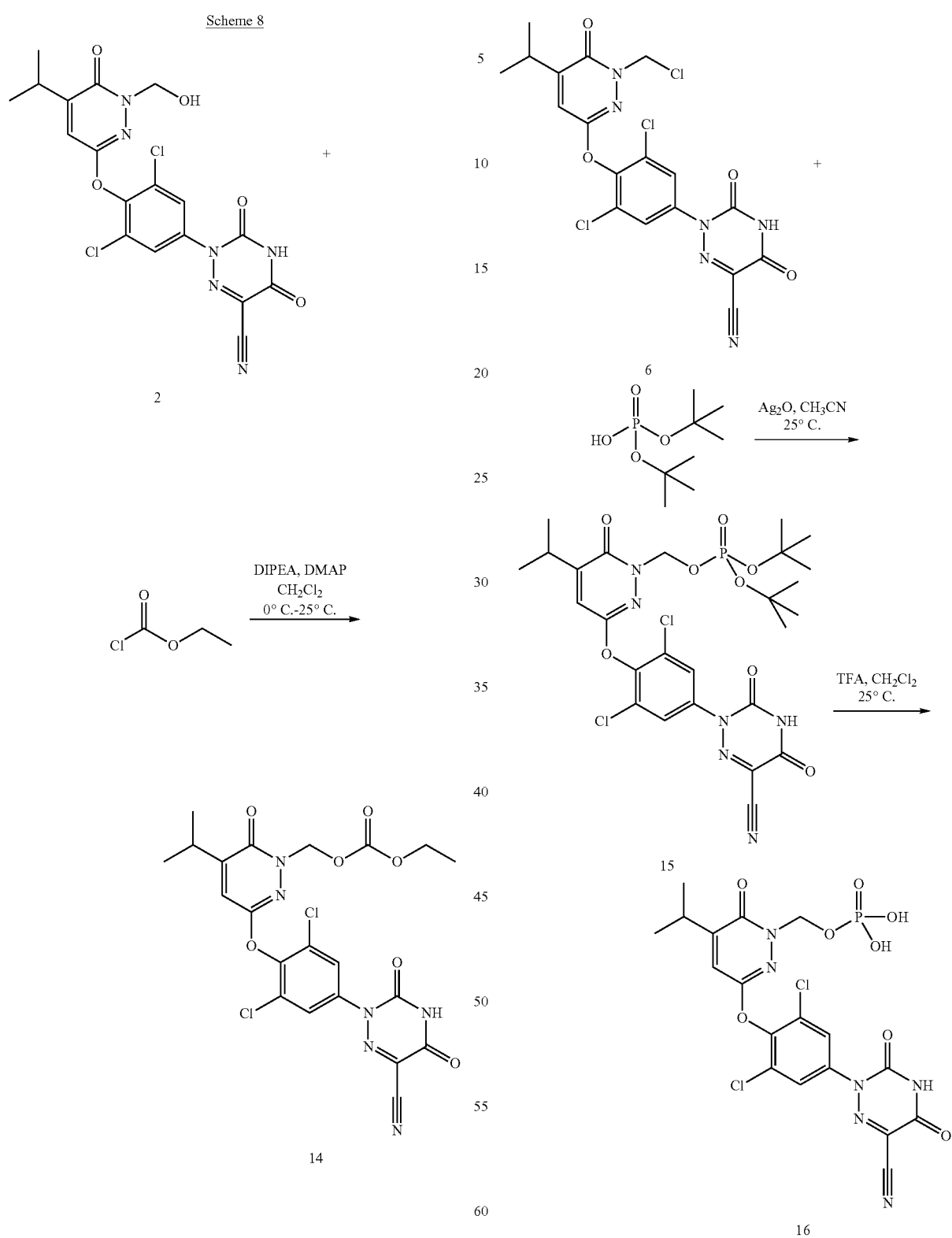

Compound 14 was synthesized following the reaction outlined in scheme 8. Compound 2 was treated with base and 4-N,N-dimethylaminopyridine followed by ethyl chloroformate to give compound 14 (see for example, Dunn, J. P., et. al. PCT Int. Appl. (2005) WO 090317A1).

Compound 16 was synthesized following the reaction outlined in scheme 9. The chloride of compound 6 was displaced with phosphoric acid di-tert-butyl ester in the presence of silver (I) oxide (see for example, Ermolenko, L., et. al., *J. Org.*

Chem, 2006, 71(2), 693-703). Phosphoric acid di-tert-butyl ester was synthesized following literature precedence (see for example, Zwierzak, A., et. al., *Tetrahedron*, 1971, 27, 3163-3170). The tert-butyl protecting groups were then removed using standard acidic conditions to give compound 16 (see for example, Theodora W. Greene and Peter G. M. Wuts, Protective Groups in Organic Synthesis (2nd Ed. 1991), John Wiley and Sons, Inc.).

The compounds of formula (I) are thyroid hormone prodrugs. The TR/RXR/GRIP Assay was used to test a compound of formula (I), as shown in the Examples below. Thus, the tested prodrug compound was not a thyroid hormone receptor agonist, having an EC50 of >50 μM. However, upon conversion either in vitro or in vivo to the compound of formula (Ia), compounds of formula (I) were shown to exhibit similar, and in some cases improved, in vivo properties.

The invention will now be further described in the Examples below, which are intended as an illustration only and do not limit the scope of the invention.

EXAMPLES

Example 1

2-[3,5-Dichloro-4-(1-hydroxymethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile

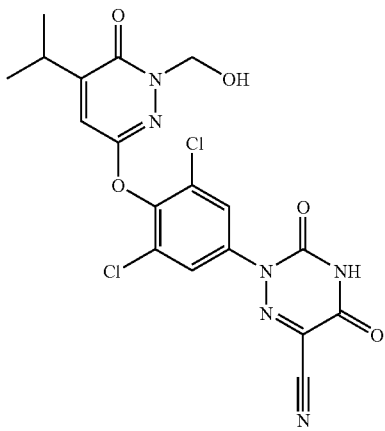

A solution of 2-[3,5-dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile (2.0 g, 4.60 mmol) in methanol (30 mL) was treated with a solution of 37% aqueous formaldehyde (7.5 mL, 100.72 mmol). The resulting mixture was heated to 100° C. for 18 h. At this time, the reaction mixture was cooled to 25° C. and was diluted with water. The resulting precipitate was collected by filtration, was washed with water and was dried in vacuo to afford 2-[3,5-dichloro-4-(1-hydroxymethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (1.97 g, 92%) as a light yellow solid. ES+-HRMS m/e calcd for $C_{18}H_{14}N_6O_5Cl_2$ (M+H+) 465.0476, found 465.0475.

Example 2

Acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester

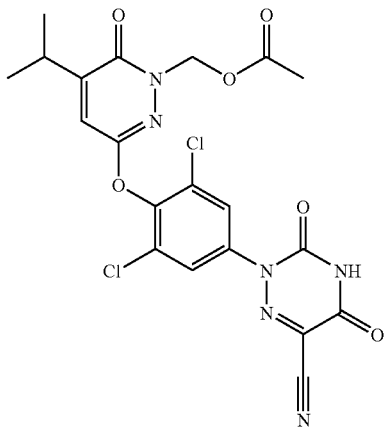

A solution of 2-[3,5-dichloro-4-(1-hydroxymethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (200 mg, 0.43 mmol), N,N-diisopropylethylamine (0.23 mL, 1.29 mmol) and 4-N,N-dimethylaminopyridine (25.8 mg, 0.21 mmol) in methylene chloride (3.0 mL) cooled to 0° C. was treated with acetyl chloride (33.5 μL, 0.47 mmol). The reaction mixture was warmed to 25° C. over 3.5 h. The reaction mixture was then warmed to 40° C. and stirred overnight. At this time, the reaction mixture was cooled to 25° C. and then partitioned between methylene chloride (100 mL) and water (100 mL). The organics were then washed with a 1N aqueous hydrochloric acid solution (3×100 mL), water (1×100 mL) and a saturated aqueous sodium chloride solution (1×100 mL). The organics were dried over magnesium sulfate, filtered, rinsed and concentrated in vacuo. ISCO CombiFlash chromatography (40 g, 0.5-4.0% methanol/methylene chloride) afforded acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (45.9 mg, 21%) as a yellow solid. ES+-HRMS m/e calcd for $C_{20}H_{16}N_6O_6Cl_2$ (M+H+) 507.0581, found 507.0582.

Example 3

2,2-Dimethyl-propionic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2 from 2,2-dimethyl-propionyl chloride: 2,2-dimethyl-propionic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a yellow solid (58.5 mg, 25%); ES+-HRMS m/e calcd for $C_{23}H_{22}N_6O_6Cl_2$ (M+H+) 549.1051, found 549.1049.

Example 4

Butyric acid 3-[2,6-Dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2 from butyryl chloride: butyric acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a yellow solid (55 mg, 24%); ES$^+$-HRMS m/e calcd for $C_{22}H_{20}N_6O_6Cl_2$ (M+H$^+$) 535.0894, found 535.0891.

Example 5

Isobutyric acid 3-[2,6-Dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2, from isobutyryl chloride: isobutyric acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a yellow solid (91.7 mg, 40%); ES$^+$-HRMS m/e calcd for $C_{22}H_{20}N_6O_6Cl_2$ (M+H$^+$) 535.0894, found 535.0891

Example 6

Morpholine-4-carboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2, from morpholine-4-carbonyl chloride: morpholine-4-carboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as an off-white solid (34.2 mg, 14%); ES$^+$-HRMS m/e calcd for $C_{23}H_{21}N_7O_7Cl_2$ (M+H$^+$) 578.0953, found 578.0952.

Example 7

Benzoic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2, from benzoyl chloride: benzoic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a yellow solid (109.1 mg, 45%); ES$^+$-HRMS m/e calcd for $C_{25}H_{18}N_6O_6Cl_2$ (M+H$^+$) 569.0738, found 569.0736.

Example 8

Pyrazine-2-carboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2, from pyrazine-2-carbonyl chloride, prepared as described in *J. Med. Chem.*, 1995, 38(20), 3902-3907: pyrazine-2-carboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a light yellow solid (141.2 mg, 57%); ES$^+$-HRMS m/e calcd for $C_{23}H_{16}N_8O_6Cl_2$ (M+H$^+$) 571.0643, found 571.0641.

Example 9

Pyrimidine-5-carboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2, from pyrimidine-5-carbonyl chloride, prepared as described in *J. Heterocyclic Chem.*, 1985, 22, 437-439: pyrimidine-5-carboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a white solid (54.2 mg, 21%); ES$^+$-HRMS m/e calcd for $C_{23}H_{16}N_8O_6Cl_2$ (M+H$^+$) 571.0643, found 571.0642.

Example 10

Propionic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2 from propionyl chloride: propionic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a yellow solid (201.3 mg, 60%); ES$^+$-HRMS m/e calcd for $C_{21}H_{18}N_6O_6Cl_2$ (M+H$^+$) 521.0738, found 521.0735.

Example 11

(4-Methyl-piperazin-1-yl)-acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2 from the dihydrochloride salt of (4-methyl-piperazin-1-yl)-acetyl chloride: (4-methyl-piperazin-1-yl)-acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a yellow solid (37.4 mg, 14.4%); ES$^+$-HRMS m/e calcd for $C_{25}H_{26}N_8O_6Cl_2$ (M+H$^+$) 605.1425, found 605.1427.

Example 12

Morpholin-4-yl-acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 2 from morpholin-4-yl-acetyl chloride: morpholin-4-yl-acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1- ylmethyl ester was obtained as an off-white solid (66.8 mg, 26%); ES$^+$-HRMS m/e calcd for $C_{24}H_{23}N_7O_7Cl_2$ (M+H$^+$) 592.1109, found 592.1110.

Example 13

Succinic acid mono-{3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl}ester

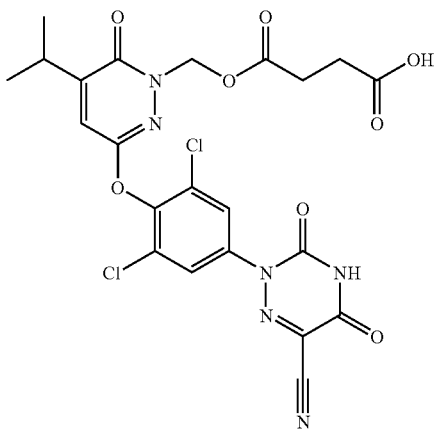

A solution of 2-[3,5-dichloro-4-(1-hydroxymethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (200 mg, 0.42 mmol), 4-N,N-dimethyaminopyridine (2.6 mg, 0.02 mmol) and succinic anhydride (47 mg, 0.47 mmol) in methylene chloride (2.53 mL) at 25° C. was treated with N,N-diisopropylethylamine (0.17 mL, 0.98 mmol). The reaction mixture was stirred at 25° C. for 3.5 h. At this time, the reaction mixture was poured onto a saturated aqueous ammonium chloride solution (100 mL) and was then extracted with a 90/10 methylene chloride/methanol solution (3×100 mL). The pH of the aqueous layer was brought to pH=2 with a few drops of a 2N aqueous hydrochloric acid solution and was then extracted with a 90/10 methylene chloride/methanol solution (1×100 mL). The combined organics were dried over sodium sulfate, filtered, rinsed and concentrated in vacuo. ISCO CombiFlash chromatography (12 g, 0.5-4% methanol/methylene chloride) followed by supercritical fluid chromatography (Daicel OJ column, 30% methanol) afforded succinic acid mono-{3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl}ester (57 mg, 24%) as a light tan solid. ES$^+$-HRMS m/e calcd for $C_{22}H_{18}N_6O_8Cl_2$ (M+H$^+$) 565.0636, found 565.0633.

Example 14

Pyridin-3-yl-acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester

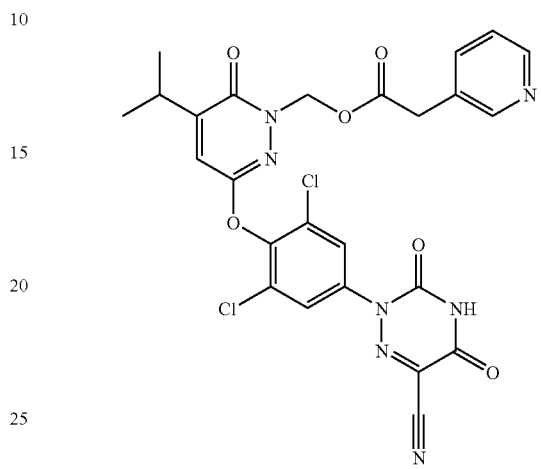

A solution of pyridin-3-yl-acetic acid hydrochloride salt (57.3 mg, 0.33 mmol) in methylene chloride (1.84 mL) was treated with N,N,N',N'-tetramethyl-O—(N-succinimidyl) uronium tetrafluoroborate (119 mg, 0.39 mmol) and N,N-diisopropylethylamine (0.17 mL, 0.99 mmol). The resulting solution was stirred at 25° C. for 2.5 h. At this time, 2-[3,5-dichloro-4-(1-hydroxymethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (200 mg, 0.42 mmol) was added to the reaction. The reaction mixture was stirred at 25° C. for 18 h. At this time, the reaction mixture was diluted with methylene chloride (50 mL) and washed with water (3×150 mL). The organics were dried over sodium sulfate, filtered, rinsing with methylene chloride and concentrated in vacuo. Biotage flash chromatography (40S, 1-4% methanol/methylene chloride) followed by supercritical fluid chromatography (Daicel OD column, 60% methanol) afforded pyridin-3-yl-acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (43.2 mg, 22%) as a yellow solid. ES$^+$-HRMS m/e calcd for $C_{25}H_{19}N_7O_6Cl_2$ (M+H$^+$) 584.0847, found 584.0848.

Example 15

Isonicotinic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester Using the method described in Example 14 from 2-[3,5-dichloro-4-(1-hydroxymethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile and isonicotinic acid: isonicotinic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester was obtained as a light

Example 16

(S)-2-Amino-3-methyl-butyric acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester hydrochloride salt

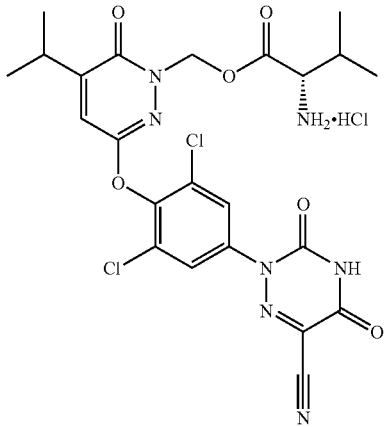

a. A solution of 2-[3,5-dichloro-4-(1-hydroxymethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (600 mg, 1.29 mmol) in tetrahydrofuran (9.0 mL, 0.14 M) cooled to 0° C. was treated with thionyl chloride (0.28 mL, 3.84 mmol). The reaction mixture was allowed to slowly warm to 25° C. The reaction mixture was stirred at 25° C. overnight. At this time, the reaction mixture was concentrated in vacuo. The residue was taken up in benzene and was re-concentrated twice to afford 2-[3,5-dichloro-4-(1-chloromethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile as a yellow solid. The material was used without further purification.

b. A solution of 2-[3,5-dichloro-4-(1-chloromethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (0.64 mmol) in acetonitrile at 25° C. was treated with L-2-tert-butoxycarbonylamino-3-methyl-butyric acid (147 mg, 0.67 mmol) followed by silver (I) oxide (155.4 mg, 0.67 mmol). The reaction mixture was stirred at 25° C. in the dark for 2 d. At this time, the reaction mixture was filtered through a pad of celite® and was rinsed with a solution of 90/10 methylene chloride/methanol (1×100 mL). The filtrate was then concentrated in vacuo. ISCO CombiFlash chromatography (40 g, 0.5-4% methanol/methylene chloride) afforded L-2-tert-butoxycarbonylamino-3-methyl-butyric acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (246.1 mg, 57.5%) as a tan solid. This material was used without further purification.

c. A solution of L-2-tert-butoxycarbonylamino-3-methyl-butyric acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (75.8 mg, 0.114 mmol) in ethyl acetate (570 µL) at 25° C. was treated with a solution of 4M hydrochloric acid in 1,4-dioxane (0.18 mL, 0.75 mmol). The reaction solution was stirred at 25° C. for 4 h. At this time, the cloudy reaction mixture was filtered through filter paper which was washed with ethyl acetate (0.5 mL). The filtrate was treated dropwise with diethyl ether (2.0 mL). The resulting white precipitate was triturated with diethyl ether (3×2 mL) and then dried in vacuo. The resulting solid was then slurried with ethanol (3×1.5 mL), concentrated and dried in vacuo to afford (S)-2-amino-3-methyl-butyric acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester hydrochloride salt (49.8 mg, 72.6%) as an off-white solid. ES$^+$-HRMS m/e calcd for $C_{23}H_{23}N_7O_6Cl_2$ (M+H$^+$) 564.1160, found 564.1164.

Example 17

(2S, 3S)-2-Amino-3-methyl-pentanoic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester hydrochloride salt Using the method described in Example 16b and c, from 2-[3,5-dichloro-4-(1-chloromethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile and L-2-tert-butoxycarbonylamino-3-methyl-pentanoic acid: (2S, 3S)-2-amino-3-methyl-pentanoic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester hydrochloride salt was obtained as an off-white solid (35.8 mg, 50.9%); ES$^+$-HRMS m/e calcd for $C_{24}H_{25}N_7O_6Cl_2$ (M+H$^+$) 578.1316, found 578.1315.

Example 18

Cyclopentanecarboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester

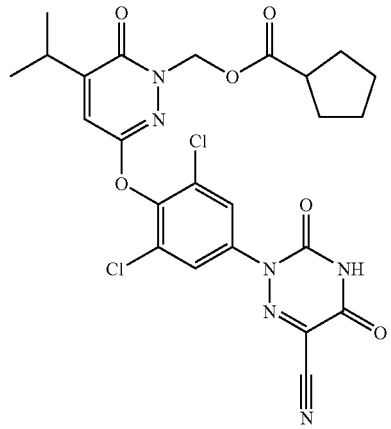

A solution of 2-[3,5-dichloro-4-(1-chloromethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (0.64 mmol) in acetonitrile (18 mL) at 25° C. was treated with cyclopentanecarboxylic acid (73.4 µL, 0.67 mmol) followed by silver (I) oxide (155.4 mg, 0.67 mmol). The reaction mixture was stirred at 25° C. in the dark for 3 d. At this time, the reaction was filtered through a pad of celite® and was rinsed with a solution of 90/10 methylene chloride/methanol (1×100 mL). The filtrate was then concentrated in vacuo. Biotage flash chromatography (40S, 0.5-1.25% methanol/methylene chloride) followed by reverse phase chromatography (Pursuit C-18 column, acetonitrile gradient with trifluoroacetic acid) followed by lyophilization afforded cyclopentanecarboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (75.7 mg, 21%) as an off-white solid. ES$^+$-HRMS m/e calcd for $C_{24}H_{22}N_6O_6Cl_2$ (M+Na$^+$) 583.0870, found 583.0871.

Example 19

(S)-2-Amino-propionic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester hydrochloride salt

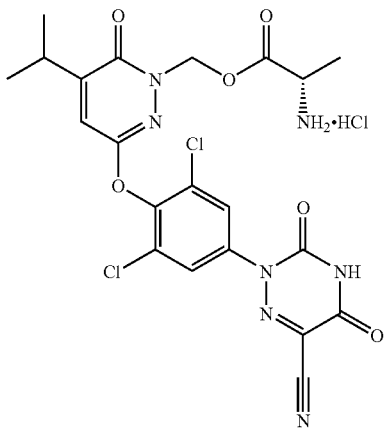

A solution of L-2-tert-butoxycarbonylamino-propionic acid (2.83 g, 15.0 mmol) in a 7:3 ethanol/water solution (75 mL) at 25° C. was treated dropwise with a 1 M aqueous cesium carbonate solution until the pH of the solution was between 6.4 and 6.7. At this time, the reaction solution was concentrated in vacuo and dried under high vacuum to afford L-2-tert-butoxycarbonylamino-propionic acid cesium salt as a white solid (3.36 g, 69%). This material was used without further purification.

b. A solution of L-2-tert-butoxycarbonylamino-propionic acid cesium salt (1.50 g, 4.67 mmol) in N,N-dimethylformamide (14 mL) at 25° C. in a darkened fume hood was treated dropwise over 45 min via an addition funnel with bromochloromethane (31 mL, 464.56 mmol). The reaction mixture was then wrapped with aluminum foil and was stirred at 25° C. for 18 h. At this time, the reaction was filtered to remove a white precipitate. The precipitate was washed with methylene chloride. The filtrate was concentrated in vacuo and then dried under high vacuum to afford L-2-tert-butoxycarbonylamino-propionic acid chloromethyl ester (1.0 g, 90%) as a yellow oil. The material was used without further purification.

c. A solution of 2-[3,5-dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile (0.63 g, 1.45 mmol), L-2-tert-butoxycarbonylamino-propionic acid chloromethyl ester (0.38 g, 1.60 mmol) in N,N-dimethylformamide (2.4 mL) at 25° C. was treated with triethylamine (0.41 mL, 2.91 mmol). The reaction mixture was heated to 50° C. for 18 h in a sealed reaction vessel. At this time, the reaction mixture was diluted with methylene chloride (150 mL) and was washed with water (3×250 mL). The combined organics were dried over magnesium sulfate, filtered, rinsed and concentrated in vacuo. ISCO CombiFlash chromatography (40 g, 0.5-5.0% methanol/methylene chloride) afforded L-2-tert-butoxycarbonylamino-propionic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (153.3 mg, 17%) as a brown solid.

d. A solution of L-2-tert-butoxycarbonylamino-propionic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (153.3 mg, 0.24 mmol) in ethyl acetate (1.2 mL) at 25° C. was treated with a 4M solution of hydrochloric acid in 1,4-dioxane (0.4 mL, 1.60 mmol). The reaction mixture was stirred at 25° C. for 4.3 h. At this time, another portion of a 4M solution of hydrochloric acid in 1,4-dioxane (0.4 mL, 1.60 mmol) was added. The reaction mixture was stirred at 25° C. for 18 h. At this time, the reaction mixture was diluted with diethyl ether (3 mL) and was then stirred for 2 min. The resulting solids were collected by filtration to afford a brown solid (116 mg). The solid was purified by supercritical fluid chromatography (Whelk-O1 R,R column 30% methanol) to afford (S)-2-amino-propionic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester hydrochloride salt (28.3 mg, 21%) as a light yellow solid. ES$^+$-HRMS m/e calcd for $C_{21}H_{19}N_7O_6Cl_2$ (M+H$^+$) 536.0847, found 536.0843.

Example 20

Carbonic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester ethyl ester

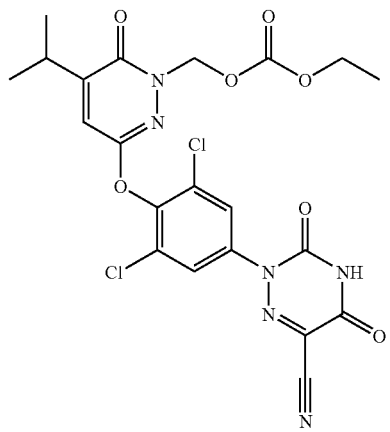

A solution of 2-[3,5-dichloro-4-(1-hydroxymethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (200 mg, 0.43 mmol), 4-N,N-dimethyaminopyridine (25.3 mg, 0.21 mmol), N,N-diisopropylethylamine (0.23 mL, 1.29 mmol), in methylene chloride (3 mL) at 0° C. was treated with ethyl chloroformate (45 µL, 0.47 mmol). The reaction was stirred at allowed to gradually warm to 25° C. and was stirred at 25° C. for 48 h. At this time, the reaction mixture was diluted with methylene chloride (100 mL) and was washed with water (3×100 mL). The combined organics were washed with a saturated aqueous sodium chloride solution (1×100 mL), dried over magnesium sulfate, filtered, rinsed and concentrated in vacuo. ISCO CombiFlash chromatography (40 g, 1-10% methanol/methylene chloride) followed by reverse phase chromatography (Pursuit C-18 column, acetonitrile gradient with ammonium acetate) afforded carbonic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester ethyl ester (89.9 mg, 39%) as a white solid. ES$^+$-HRMS m/e calcd for $C_{21}H_{18}N_6O_7Cl_2$ (M+H$^+$) 537.0687, found 537.0686.

Example 21

Phosphoric acid mono-{3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl}ester

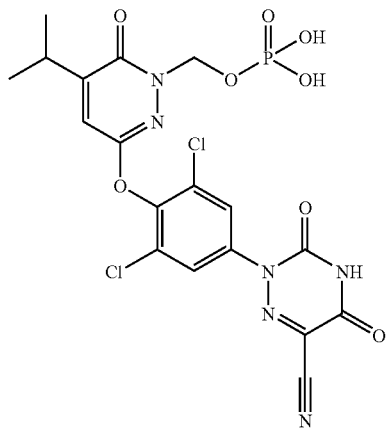

A solution of 2-[3,5-dichloro-4-(1-chloromethyl-5-isopropyl-6-oxo-1,6-dihydro-pyridazin-3-yloxy)-phenyl]-3,5-dioxo-2,3,4,5-tetrahydro-[1,2,4]triazine-6-carbonitrile (0.64 mmol) in acetonitrile (18 mL) at 25° C. was treated with methyl-phosphonic acid di-tert-butyl ester (271.8 mg, 1.29 mmol) followed by silver (I) oxide (155.9 mg, 0.67 mmol). The reaction mixture was stirred at 25° C. in the dark for 18 h. At this time, the reaction was filtered through a pad of celite® and was rinsed with a solution of 90/10 methylene chloride/methanol (1×100 mL). The filtrate was then concentrated in vacuo. Biotage chromatography (40S, 1.0-3.5% methanol/methylene chloride) followed by supercritical fluid chromatography afforded phosphoric acid di-tert-butyl ester 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (48 mg, 21%) as an impure, light yellow solid. The material was used without further purification.

b. A solution of phosphoric acid di-tert-butyl ester 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester (44.0 mg, 0.067 mmol) in methylene chloride (1.0 mL, 0.067M) at 25° C. was treated with trifluoroacetic acid (0.2 mL). The reaction mixture was stirred at 25° C. for 20 min. At this time, the reaction mixture was concentrated in vacuo, azeotropically dried with benzene and concentrated from absolute ethanol followed by lyophilization from acetonitrile and water to afford phosphoric acid mono-{3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl}ester (31.4 mg, 86%) an off-white solid. Present in the product was 0.95 moles of residual ammonium from the ammonium acetate used in the supercritical fluid purification of the precursor. ES$^+$-HRMS m/e calcd for $C_{18}H_{15}N_6O_8PCl_2$ (M+Na$^+$) 566.9958, found 566.9962.

Example 22

TR/RXR/GRIP Assay

In this Example, a TR/RXR/GRIP assay was used to test representative compounds of formula (I). Abbreviations used: H6-TRβ, ligand binding domain of thyroid hormone receptor β with hexa His tag; H6-TRα ligand binding domain of thyroid hormone receptor α with hexa His tag; EE-RxRα, ligand binding domain of retinoid X receptor with EE-tag; APC, allophycocyanin; BSA, bovine serum albumin; DMSO, dimethyl sulfoxide.

Materials

The ligand binding domain (amino acids 148-410) of thyroid hormone receptor β (H6-TRβ and the ligand binding domain (amino acids 202-461) of thyroid hormone receptor α (H6-TRα) were cloned into an *E. coli* expression vector pET28a (Novagen, Milwaukee, Wis.) which contained a N-terminal hexaHis sequence. The resulting recombinant hexaHis tagged proteins were produced in *E. coli* BL21 (DE3) cells. Cells were grown in Terrific Broth (in-house prepared medium of Bacto tryptone (3.3%, w/v), Difico yeast extract (2.0%, w/v) and NaCl (0.5%, w/v)) using shake flasks with a 24 hour induction in 0.2 mM IPTG at 25° C., harvested and lysed with five volumes of Buffer A (0.05M Tris, 0.3M NaCl, 1%W/V Betaine, 0.01M imidazole, 0.02M β-mercapto ethanol, pH 8.0). Lysozyme (1.0 mg/ml, Sigma) and Complete Protease Inhibitor Cocktail (Roche Diagnostics Gmbh) were added to slurry and solution sonicated for one min five times at 4° C. The suspension was centrifuged in a Ti45 Beckmann rotor for two hours at 127,300 RCF and the supernatant was loaded onto NiNTA Agarose (Qiagen 30210) column. After washing with Buffer A, H6-TRβ or H6-TRα was eluted with Buffer A containing 0.25M imidazole.

The ligand binding domain of human retinoid X receptor (amino acids 225-462) (RxRα) was engineered with N-terminal His6 and EE (EFMPME) tags, a thrombin cleavage site between the His6 and EE sequences, and cloned into PACYC vector. The resulting His6-EE-tagged protein was produced in *E. coli* cells. Cells were grown using shake flasks with an 18 hour induction in 0.1 mM IPTG at 18° C., harvested and suspended with five volumes of Buffer B (0.025M Tris, 0.3M NaCl, 0.02 M imidazole, 0.01M β-mercaptoethanol, pH 8.0). Lysozyme (0.2 mg/ml, Sigma) and Complete Protease Inhibitor Cocktail (Roche Diagnostics Gmbh) were added and stirred for 30 min. at 4° C. The suspension was sonicated for 30 seconds, five times, at 4° C. The suspension was centrifuged for 20 min. at 12,000 RCF. The supernatant was filtered by 0.45 µm pore size membrane and 0.5% NP-40 was added. The His6-tagged protein was bound to and eluted from NiNTA metal-affinity resin (Qiagen, Valencia, Calif.). The protein was concentrated and dialyzed.

The His6 tag was removed from EE-RxRα by thrombin digestion, using 10 units thrombin (Pharmacia, Piscataway, N.J.) per mg protein and incubating for 2 hours at 25° C. Removal of thrombin was done batch-wise using Benzamidine-Sepharose 6B (Pharmacia, Piscataway, N.J.). The protein was concentrated and dialyzed. This protein was used in the coactivator peptide recruitment assay.

Europium-conjugated anti-hexa His antibody and APC-conjugated streptavidin were purchased from PerkinElmer Life and Analytical Sciences.

TRβ/RXR/GRIP Coactivator Peptide Recruitment Assay

Thirty microliters of H6-TRβ(50 nM) in 50 mM Hepes, pH 7.0, 1 mM DTT, 0.05% NP40 and 0.2 mg/ml BSA (Binding Buffer) were mixed with an equal volume of EE-RxRα (50 nM) in Binding Buffer. Six microliters of T3 (0-14.8 uM) or test compound (0-1.2 mM) in DMSO was then added and the solution incubated at 37° C. for 30 min. Thirty microliters of biotin-GRIP peptide (Biotin-Aca-HGTSLKEKHKILHR-LLQDSSSPVDL-CONH2) (100 nM) in 30 μl of Binding Buffer plus 5% DMSO was then added and the solution incubated at 37° C. for 30 min. Thirty microliters of solution containing 12 nM europium-conjugated anti-hexa His antibody and 160 nM APC-conjugated streptavidin in 50 mM Tris, pH 7.4, 100 mM NaCl and 0.2 mg/ml BSA was added and the solution incubated at 4° C. for over night. An aliquot (35 ul/sample) was transferred to 384-well black microtiter plates. The HTRF signal was read on the Victor 5 reader (PerkinElmer Life and Analytical Sciences).

TRα/RXR/GRIP Coactivator Peptide Recruitment Assay

The assay protocol is essentially the same as that of TRβ/RXR/GRIP coactivator peptide recruitment assay as described above except that 125 nM of H6-TRα, 125 nM of EE-RxRα and 250 nM of biotin-GRIP were used.

As shown in the Table below, the tested compounds are thyroid hormone receptor agonists, with $EC_{50}$ values from the THR-beta/RXR/GRIP recruitment assay:

TABLE 1

| Compound | THR-beta/RXR/GRIP Recruitment assay $EC_{50}$ (μM) | Systematic Name |
|---|---|---|
| Ia | 0.1918 | 2-[3,5-Dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile |
| Example 5 | >57.6 | Isobutyric acid 3-[2,6-Dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester |

Example 23

Cell Culture

Caco-2 cells were grown in Minimum Essential Medium (MEM), containing 10% fetal bovine serum, 1% non-essential amino acids, 100 units/ml penicillin and 100 μg/ml streptomycin. They were incubated at 37° C. in a humidified atmosphere of 5% $CO_2$. Culture medium was changed every other day. Caco-2 cells were passed once per week by trypsinization.

Efflux Transport Assay

Caco-2 cells were seeded at a density of $4.55 \times 10^5$ cells/$cm^2$. Caco-2 cells were incubated for 7 days at 37° C. Medium was changed every two or three days for Caco-2 cells. Prior to the experiment, cells were equilibrated with transport medium [HBSS (pH 7.4) containing 10 mM HEPES] at 37° C. for 30 min. The transepithelial electrical resistance (TEER) of cell monolayers was measured using "chopstick" electrodes (World Precision Instruments, Sarasota, Fla.). Caco-2 cell monolayers with TEER values>500 were used for the assays.

Samples were prepared in transport medium containing 1% DMSO. Test compounds were applied to the donor chamber at 10 μM. Plates were incubated at 37°C while shaking at 90 rpm. Samples were taken at 60 and 120 min from the receiver chamber. TEER values were measured at 5 minutes before the final sampling time point. Samples were mixed with 2 volumes of acetonitrile and centrifuged at 3,500 rpm at 4° C. for 10 min. The supernatant was diluted with 1 volume of water containing 1% acetic acid. Samples were analyzed by LC/MS. Standard serial dilutions were prepared manually at 10, 50, 250, 1,250 and 2,500 nM.

Data Analysis and Calculations

The apparent permeability ($P_{app}$) was calculated with the following equation:

$$P_{app} = \frac{dC}{dt} \frac{V}{C_0 A}$$

where C is the receiver chamber drug concentration, t is time in second, V is the volume of the receiver chamber, $C_o$ is the initial drug concentration in the donor chamber and A is the surface area of the filter.

TABLE 2

Permeability from Caco-2 cells

| Compound | Input (μM) | $P_{app}$ ($10^{-7}$ cm/sec) | Mass Balance* |
|---|---|---|---|
| Example 5 | 40.2 | 88.7 ± 6.3 | 47.9 |
| Example 2 | 27.2 | 45.8 ± 7.4 | 71.0 |
| Example 12 | 40.5 | 17.5 ± 6.5 | 95.0 |
| Example 6 | 53.4 | 12.4 ± 2.4 | 101.5 |
| Example 8 | 61.0 | 9.2 ± 1.1 | 92.8 |
| Example 13 | 58.1 | 2.3 ± 0.6 | 84.4 |

*The mass balance was calculated from pro-drug only and does not include converted drug.

Example 24

A single dose (10 mg/kg) PO (intubation) PK in rats (3 animals) was performed with the compound of Example 5 using a 2% Klucel, 0.1% Tween 80 in water formulation.

Analytical Method:

Aliquots (0.05 mL) of rat plasma were protein precipitated with acetonitrile. The extracts were diluted with an equal volume of water and injected onto the LC/MS/MS system. The linear range of the method for the compound of formula (Ia) was 1.0 to 1000 ng/mL. Assay performance, as monitored by the analysis of QC samples analyzed along with the samples, was as shown in table 3.

TABLE 3

| Parameter | Units | Compound Ia | Example 5 |
|---|---|---|---|
| Dose | mg/kg | 10 | 10 |
| AUC Extrap | ng * Hours/mL | 28,663 | 50,825 |
| Cmax | ng/mL | 3,070 | 5,530 |
| Tmax | Hours | 5 | 3 |
| F | % | 38 | 70 |

The compound of Example 5, prodrug of compound Ia, was dosed orally to rats at 10 mg/kg. Both the prodrug and parent, compound Ia, were monitored. However, only the parent was detected. The bioavailability of the parent after dosing with the prodrug was almost 2 fold higher than that obtained after dosing with parent. Absorption of the prodrug was faster than the parent. Variability in exposure of the parent after dosing with the prodrug was improved over that obtained after dosing with parent.

Example 25

A single dose (10 mg/kg) PO (intubation) PK in dogs (3 animals) was performed with the compound of Example 5 using a 2% Klucel, 0.1% Tween 80 in water formulation.

Analytical Method:

Aliquots (0.05 mL) of dog plasma were mixed with 0.050 mL of pH 7.4 phosphate buffered saline and a 0.010 mL aliquot of a stable labeled internal standard working solution. Each of the samples was then extracted with 0.500 mL of ethyl acetate. A 0.350 mL aliquot of each of the sample extract supernatant was transferred to an injection block and evaporated to dryness using the turbovap evaporator. The sample was then reconstituted with 0.200 mL of a 1:1 mixture of water:acetonitrile containing 0.1% acetic acid. A 0.020 mL sample from each well was injected onto the LC/MS/MS system. The linear range of the method for the compound of formula (Ia) was 5.0 to 5000 ng/mL. Assay performance, as monitored by the analysis of QC samples analyzed along with the samples, was as shown in table 4.

TABLE 4

| Parameter | Units | Compound Ia | Example 5 |
|---|---|---|---|
| Dose | mg/kg | 10 | 10 |
| AUC | ng * Hours/mL | 2,936 | 2,919 |
| Cmax | ng/mL | 364 | 530 |
| Tmax | Hours | 3 | 2 |
| F | % | 13 (9-17) | 13 (10-16) |
| F % CV | | 32 | 24 |

The compound of Example 5 was dosed orally to dogs at 10 mg/kg. Both the prodrug and parent, compound Ia, were monitored. However, only the parent was detected. The bioavailability of parent in dog after dosing with the compound of Example 5 was comparable to that obtained when dosed with parent. However, the variability in the oral exposure was reduced when dosed with the compound of Example 5 as compared when dosed with parent.

* * *

It is to be understood that the invention is not limited to the particular embodiments of the invention described above, as variations of the particular embodiments may be made and still fall within the scope of the appended claims.

What is claimed is:

1. A compound of formula (I):

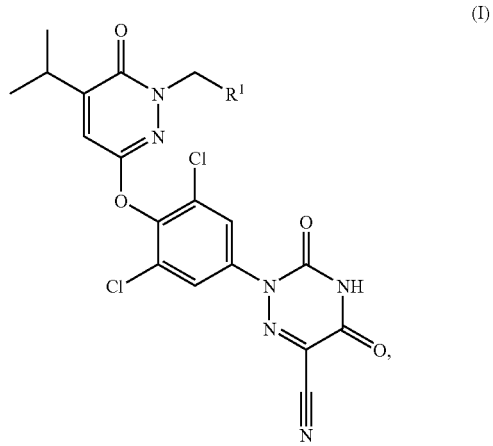

wherein:
R¹ is —OH, O-linked amino acid, —OP(O)(OH)₂ or —OC(O)—R²;
R² is lower alkyl, alkoxy, alkyl acid, cycloalkyl, heterocycloalkyl, —(CH₂)ₙ-heterocycloalkyl, aryl, heteroaryl, or —(CH₂)n-heteroaryl; and
n is 0 or 1;
or a pharmaceutically acceptable salt thereof.

2. The compound according to claim 1, wherein R¹ is —OC(O)—R².

3. The compound according to claim 1, wherein R¹ is —OC(O)CH[CH(CH₃)₂]NH₂, —OC(O)CH[CH(CH₃)(CH₂CH₃)]NH₂ or —OC(O)CH(CH₃)NH₂.

4. The compound according to claim 1, wherein R² is lower alkyl.

5. The compound according to claim 1, wherein R² is cycloalkyl, heterocycloalkyl, —(CH₂)ₙ-heterocycloalkyl, aryl, heteroaryl or —(CH₂)ₙ-heteroaryl.

6. The compound according to claim 1, wherein R² is cyclopentane.

7. The compound according to claim 1, wherein said cycloalkyl is substituted with lower alkyl.

8. The compound according to claim 1, wherein R² is morpholine, —CH₂-morpholine or —CH₂—N-methylpiperazine.

9. The compound according to claim 1, wherein said heterocycloalkyl or —CH₂-heterocycloalkyl is substituted with lower alkyl.

10. The compound according to claim 1, wherein R² is phenyl.

11. The compound according to claim 1, wherein R² is pyrazine, pyrimidine or pyridine.

12. The compound according to claim 1, wherein said compound is acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester.

13. The compound according to claim 1, wherein said compound is isobutyric acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester.

14. The compound according to claim 1, wherein said compound is morpholine-4-carboxylic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester.

15. The compound according to claim 1, wherein said compound is pyrazine-2-carboxylic acid 3-[2,6-dichloro-4-

(6-cyano-3,5-dioxo-4,5-dihydro-3H-[1,2,4]triazin-2-yl)-phenoxy]-5-isopropyl-6-oxo-6H-pyridazin-1-ylmethyl ester.

16. The compound according to claim 1, wherein said compound is morpholin-4-yl-acetic acid 3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl ester.

17. The compound according to claim 1, wherein said compound is succinic acid mono-{3-[2,6-dichloro-4-(6-cyano-3,5-dioxo-4,5-dihydro-3H-[1,2,4]triazin-2-yl)-phenoxy]-5-isopropyl-6-oxo-6H-pyridazin-1-ylmethyl} ester.

18. A pharmaceutical composition comprising a therapeutically effective amount of a compound according to claim 1, or a pharmaceutically acceptable salt thereof, and a pharmaceutically acceptable carrier.

\* \* \* \* \*